(12) United States Patent
Sliwa et al.

(10) Patent No.: US 11,039,882 B2
(45) Date of Patent: Jun. 22, 2021

(54) ABLATION CATHETER WITH INTERNALLY FIXED SUBELECTRODES

(71) Applicant: St. Jude Medical, Cardiology Division, Inc., St. Paul, MN (US)

(72) Inventors: John W. Sliwa, San Jose, CA (US); Stephen A. Morse, Menlo Park, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 690 days.

(21) Appl. No.: 15/783,882

(22) Filed: Oct. 13, 2017

(65) Prior Publication Data

US 2018/0104003 A1    Apr. 19, 2018

Related U.S. Application Data

(60) Provisional application No. 62/408,226, filed on Oct. 14, 2016.

(51) Int. Cl.
*A61B 18/14*    (2006.01)
*A61B 18/12*    (2006.01)
(Continued)

(52) U.S. Cl.
CPC ...... *A61B 18/1492* (2013.01); *A61B 18/1206* (2013.01); *A61B 2018/00029* (2013.01); *A61B 2018/00083* (2013.01); *A61B 2018/00101* (2013.01); *A61B 2018/00351* (2013.01); *A61B 2018/00577* (2013.01); *A61B 2018/126* (2013.01); *A61B 2018/1405* (2013.01); *A61B 2018/1467* (2013.01); *A61B 2218/002* (2013.01); *A61M 25/007* (2013.01)

(58) Field of Classification Search
CPC ... A61B 18/1492; A61B 5/042; A61B 5/0422; A61B 5/6853; A61B 2218/002; A61B 2018/1253; A61B 2018/126; A61B 2018/1467; A61B 2018/1405; A61B 2018/00083; A61B 2018/00101; A61B 2018/00029; A61B 2018/00351; A61B 2018/00357; A61B 2018/00363; A61B 2018/00577; A61B 2217/007; A61B 2017/00044; A61B 2017/00053; A61M 25/007
USPC ........... 606/41, 42, 49, 50; 607/98, 99, 101, 607/104, 105, 113, 115, 116, 122
See application file for complete search history.

(56) References Cited

U.S. PATENT DOCUMENTS

| 4,784,638 A | 11/1988 | Ghajar et al. |
| 5,685,878 A * | 11/1997 | Falwell .............. A61B 18/1492 600/372 |

(Continued)

FOREIGN PATENT DOCUMENTS

| WO | 2014113612 A1 | 7/2014 | |
| WO | WO-2014113612 A1 * | 7/2014 | ........... A61N 1/0551 |

*Primary Examiner* — Thomas A Giuliani
(74) *Attorney, Agent, or Firm* — Dykema Gossett PLLC

(57) ABSTRACT

Aspects of the present disclosure relate to electrophysiology catheters for cardiac medical procedures. More specifically, the instant disclosure relates to an ablation catheter for treating cardiac arrhythmias by ablating tissue, and having one or more subelectrodes internally fixed within the ablation catheter tip to capture electrophysiology characteristics of myocardial tissue in proximity to the one or more subelectrodes.

22 Claims, 3 Drawing Sheets

Section A-A

(51) Int. Cl.
    *A61B 18/00*    (2006.01)
    *A61M 25/00*    (2006.01)

(56) References Cited

U.S. PATENT DOCUMENTS

| | | | |
|---|---|---|---|
| 6,511,478 B1 * | 1/2003 | Burnside | A61B 18/1492 |
| | | | 600/549 |
| 7,047,068 B2 * | 5/2006 | Haissaguerre | A61B 5/0422 |
| | | | 600/466 |
| 7,998,140 B2 * | 8/2011 | McClurken | A61B 18/1442 |
| | | | 606/41 |
| 8,620,978 B2 | 12/2013 | Koyrakh | |
| 9,220,435 B2 | 12/2015 | Deno | |
| 2004/0092806 A1 * | 5/2004 | Sagon | A61B 5/0422 |
| | | | 600/374 |
| 2010/0168557 A1 * | 7/2010 | Deno | A61B 5/0422 |
| | | | 600/424 |
| 2011/0263934 A1 | 10/2011 | Aeby et al. | |
| 2018/0071017 A1 * | 3/2018 | Bar-Tal | A61B 18/1492 |

\* cited by examiner

Section A-A

ABLATION CATHETER WITH INTERNALLY FIXED SUBELECTRODES

CROSS-REFERENCE TO RELATED APPLICATION

This application claims the benefit of U.S. provisional application No. 62/408,226, filed 14 Oct. 2016, and which is hereby incorporated by reference as though fully set forth herein.

BACKGROUND a. Field

The instant disclosure relates to catheters, in particular catheters for performing medical procedures within a heart. In one embodiment, the instant disclosure relates to a catheter for diagnosing and treating cardiac arrhythmias.

b. Background

The human heart routinely experiences electrical currents traversing the cardiac tissue. Just prior to each heart contraction, the heart depolarizes and repolarizes, as electrical currents spread across the heart. In healthy hearts, there will be an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue, for example, or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, including death.

Catheters are used in a variety of diagnostic and/or therapeutic medical procedures to diagnose and correct conditions such as atrial arrhythmia, including for example, ectopic atrial tachycardia, atrial fibrillation, and atrial flutter.

Typically in a procedure, a catheter is manipulated through a patient's vasculature to, for example, a patient's heart, and carries one or more electrodes which may be used for mapping, ablation, diagnosis, or other treatments. Where an ablation therapy is desired to alleviate symptoms including atrial arrhythmia, an ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, and high-intensity focused ultrasound. As readily apparent, such an ablation treatment requires precise positioning of the ablation catheter for optimal results.

Ablation therapies are often delivered by making a number of individual ablations in a controlled fashion in order to form a lesion line. Such lesion lines are often desirable around/between the pulmonary veins in the left atrium of the heart which have been associated as the introduction point of erratic electric signals into the heart. There are devices in development or being commercialized that attempt to achieve a sufficient block of ablations with minimal applications of energy. Subelectrodes at the distal portion of a cardiac catheter can determine the efficacy of the ablation procedure. However, existing designs suffer from complexity and cost associated with the assembly techniques used to manufacture the ablation catheter tip with the subelectrodes built into the catheter tip itself.

The foregoing discussion is intended only to illustrate the present field and should not be taken as a disavowal of claim scope.

BRIEF SUMMARY

The instant disclosure relates to catheters, in particular catheters for performing medical procedures within a heart muscle. For example, the instant disclosure describes an ablation catheter for treating cardiac arrhythmias by ablating tissue, such as cardiac or renal tissue, with one or more subelectrodes built into the ablation catheter tip to capture electrophysiology characteristics of the tissue in proximity to the subelectrode.

In one exemplary embodiment of the present disclosure, an ablation catheter tip is disclosed including a tissue ablation electrode, a plurality of subelectrodes, and a biocompatible material. The tissue ablation electrode including a shell portion defining an internal cavity, and a plurality of tapered apertures extending from an interior to an exterior surface of the shell portion. Each of the subelectrodes have a conical frustum shape, and are seated within one of the plurality of tapered apertures. The taper of each aperture and subelectrode are complimentary to one another; and a biocompatible material couples the tissue ablation electrode to each of the plurality of subelectrodes along the taper. In further more specific embodiments, the ablation catheter tip further includes one or more irrigant ports at a distal portion of the ablation catheter tip, and an irrigation lumen that extends through the internal cavity of the tissue ablation electrode. In such an embodiment, the internal cavity of the tissue ablation electrode may be filled with a potting material.

In another embodiment, an ablation catheter is disclosed including a flexible catheter body having a distal portion, a tissue ablation electrode tip, and a plurality of subelectrodes. The tissue ablation electrode tip includes an internal cavity and a plurality of conical apertures. The conical apertures are distributed about an axis of the tissue ablation electrode tip, and extend from an exterior surface of the tissue ablation electrode tip into the internal cavity. The tissue ablation electrode tip is coupled to the distal portion of the flexible catheter body, and transmits energy, such as radio frequency (RF) energy, to myocardial tissue in proximity to the tissue ablation electrode to ablate the tissue. The representative catheter further includes a plurality of conical frustum shaped subelectrodes, where each of the subelectrodes are seated within one of the conical apertures in the tissue ablation electrode tip, and extend through a portion of the tissue ablation electrode tip to the internal cavity. The subelectrodes receive electrical signals indicative of one or more sensed electrophysiological characteristics of the myocardial tissue in proximity to the subelectrodes.

In another embodiment, a catheter tip is provided that includes at least an ablation electrode and at least one subelectrode. In this embodiment, the ablation electrode includes a shell defining an internal cavity, and includes at least one angled aperture formed in the shell with an internal aperture diameter larger than an external aperture diameter. The catheter tip further includes a subelectrode having a conical shape that is complementary to the angled aperture formed in the shell to enable the subelectrode to be seated into the angled aperture from the internal cavity. In this manner, the subelectrode is physically unable to move externally out of the catheter tip shell. In more particular embodiments of such a catheter tip, an electrical insulator may be positioned between the conical shape of the subelectrode and the angled aperture formed in the shell to electrically insulate the ablation electrode from the subelectrode. In yet another particular embodiment of such a catheter tip, an electrically insulating material may couple the subelectrode to the angled aperture, where the subelectrode is substantially flush with the external surface of the shell when seated into and coupled to the angled aperture. In some embodiments, the electrically insulating material is a biocompatible material, and in still other embodiments the material may also be thermally insulating.

The above discussion/summary is not intended to describe each embodiment or every implementation of the present disclosure. The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

Figure 1:
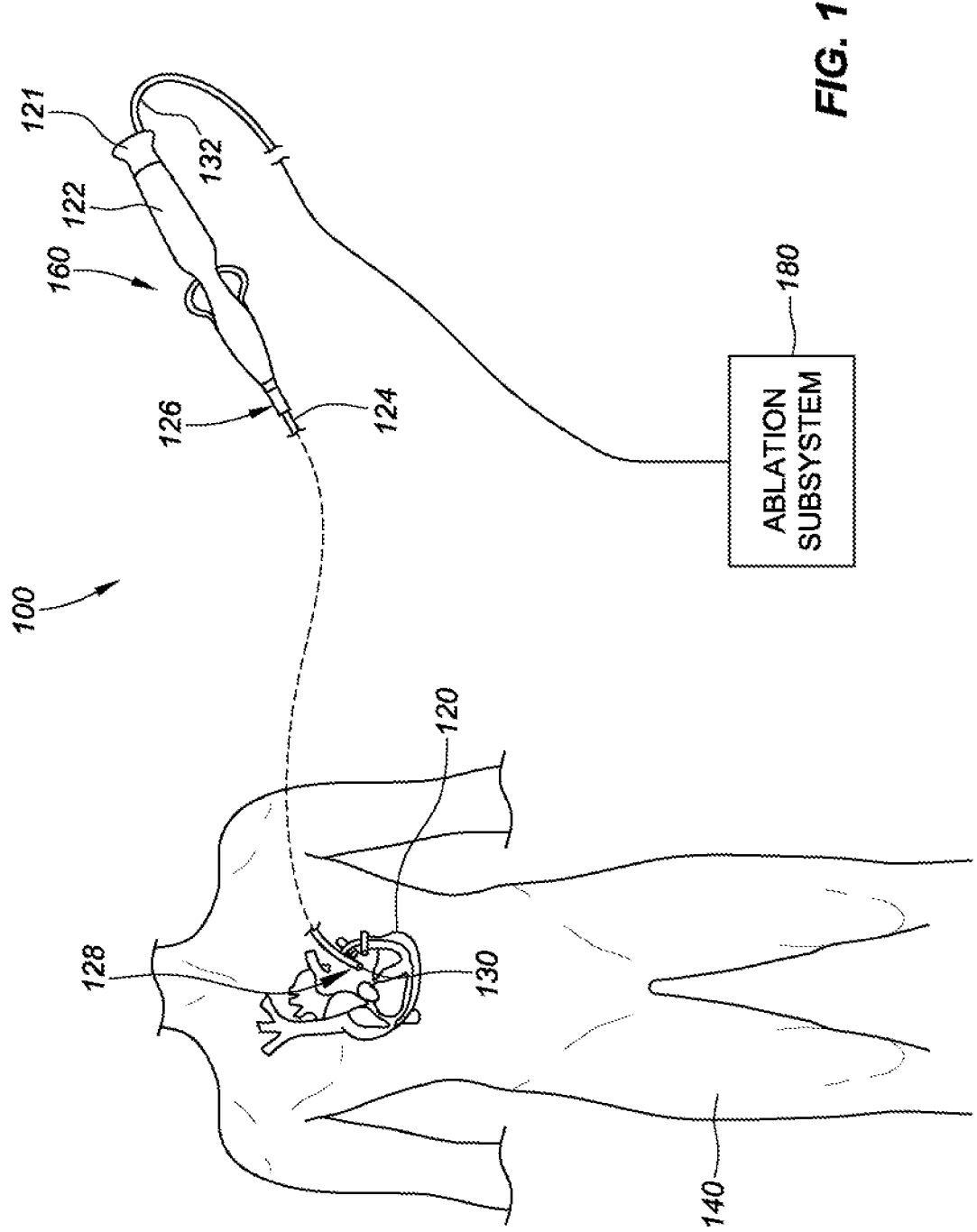
FIG. 1 is a schematic and diagrammatic view of a catheter system for performing a therapeutic medical procedure, consistent with various aspects of the present disclosure.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheters within the heart. More specifically, representative embodiments include an ablation catheter for treating cardiac arrhythmias by ablating cardiac tissue with one or more subelectrodes built into the ablation catheter tip to capture electrophysiology characteristics of the myocardial tissue in proximity to the subelectrode. Details of the various embodiments of the present disclosure are described below with specific reference to the figures.

Referring now to the drawings where like reference numerals are used to identify similar components in the various views, FIG. 1 is a schematic and diagrammatic view of a catheter ablation system 100 for performing a tissue ablation procedure. In the present exemplary embodiment, tissue 120 comprises cardiac muscle tissue within a human body 140. It should be understood, however, that the catheter ablation system can find application in connection with a variety of other tissues within human and non-human bodies, and therefore, the present disclosure is not meant to be limited to the use of the catheter ablation system in connection with only cardiac tissue and/or human bodies.

Catheter ablation system 100 can include a medical ablation catheter 160 and an ablation controller 180 for controlling an ablation therapy conducted by an ablation catheter tip 130 at a distal end 128 of the ablation catheter. The ablation controller 180 can be configured to control the application of and/or generate ablative energy including, for example, radio frequency (RF), cryoablation, laser, chemical, and high-intensity focused ultrasound. This energy can be generated at the ablation catheter tip 130, or at the ablation controller 180 and transmitted through shaft 124 via a fluid lumen (e.g., cryoablation techniques), or via electrical lumens or conductor(s) (e.g., laser, ultrasound, and radio frequency ablation techniques). The ablation controller 180 can include a graphical user interface (GUI) to allow for real-time adjustment of the ablation therapy and to indicate to a clinician important information related to the therapy. For example, the GUI can display length of time the ablation tip has been in contact with the tissue, ablation tip temperature, and other electrophysiology characteristics of the myocardial tissue in proximity to the ablation catheter tip 130.

In specific embodiments of the present disclosure, ablation controller 180 can communicate relevant ablation-related data to a catheter tip localization system (not shown), allowing a GUI of the localization system to include data on the displayed model associated with locations where ablation therapy has been administered.

In the exemplary embodiment of FIG. 1, ablation catheter 160 is provided for electrophysiological mapping, and ablation treatment of myocardial tissue within a cardiac muscle 120. Embodiments of the present disclosure utilize one or more subelectrodes within an ablation catheter tip 130 to detect electrophysiology characteristics of the myocardial tissue in proximity to the subelectrode. Of particular importance during therapies for treating cardiac arrhythmias is the determination of the source of erratic electrical impulses (such as proximate one or more of the pulmonary veins) that cause disturbances to the natural rhythm of the heart. Before, during and after the ablation therapy, the subelectrodes check the strength and frequency of the erratic electrical impulses. The efficacy of the ablation therapy is based on the reduction of these erratic electrical impulses reaching the cardiac muscle. The ablation of the myocardial tissue in contact with the ablation catheter tip causes lesions which have a higher impedance resulting in the reduced flow of electrical signals from sources outside of the cardiac muscle.

Ablation catheter 160 can include a cable connector or interface 121, a handle 122, a flexible catheter shaft 124 having a proximal end 126 and a distal end 128 (as used herein, "proximal" refers to a direction toward the end of the ablation catheter near the handle, and "distal" refers to a direction away from the handle), and an ablation catheter tip 130 coupled to the flexible catheter shaft of the ablation catheter at or near the distal end of the shaft.

In an exemplary embodiment, ablation catheter tip 130 is manipulated through vasculature of a patient 140 using handle 122 to steer one or more portions of shaft 124 and position the ablation catheter at a desired location within heart 120. In more specific embodiments, catheter ablation system 160 can include an introducer (not shown) that is similarly steerable and can be used to introduce the ablation catheter into the right or left atrium of the heart. Once the introducer is positioned at its target location within the heart, the ablation catheter can be extended through a lumen of the introducer and the steering of the ablation catheter can be used to finely position the ablation tip at a location within the heart where ablation therapy is required (e.g., circumferential ostial and antral portions of one or more pulmonary veins). The ablation catheter includes at least one ablation tip 130 at a distal portion 128 of the ablation catheter that delivers an ablation therapy (e.g., ablation electrodes, high intensity focused ultrasound ablation elements, etc.) when operated by ablation subsystem 180 to ablate the tissue in contact with the ablation tip. By tracking the location of numerous single-point ablation therapies or performing a drag lesion, a lesion line can be formed across which electrical signals are greatly impeded. Accordingly, such lesion lines result in two electrically isolated tissue portions. For example, a lesion line around a circumference of an ostial portion of a pulmonary vein will (substantially) electrically isolate the pulmonary vein from the left atrium of the cardiac muscle. Where the pulmonary vein is associated with significant introduction of erratic electrical signals into the cardiac muscle, electrical isolation (via the lesion line) will effectively alleviate cardiac arrhythmia due to the introduced electrical signal.

In various specific embodiments of the present disclosure, ablation catheter 160 can include subelectrodes and one or more positioning sensors at a distal portion 128 of shaft 124 (e.g., impedance or magnetic sensors). In such embodiments, the subelectrodes acquire electrophysiology (EP) data related to cardiac tissue 120, while the positioning sensor(s) generate positioning data indicative of the 3-D position of ablation catheter tip 130 within a coordinate system of a localization system. In further embodiments, the catheter can further include other conventional catheter components such as, for example and without limitation, steering wires and actuators, irrigation lumens and ports, pressure sensors, contact sensors, temperature sensors, additional electrodes, and corresponding conductors or leads. Importantly, it is to be understood that aspects of the present disclosure can be used in various catheter applications, and the ablation catheter embodiments presented herein are for illustrative purposes only. One of skill in the art is readily capable of modifying the various aspects of the present disclosure for use in other catheter-based medical systems.

Connector 121 provides mechanical and electrical connection(s) for one or more cables 132 extending, for example, from ablation subsystem 180 to ablation catheter tip 130 mounted on the distal end 128 of the catheter shaft 124. For example, where the ablation system utilizes cryoablation, the connector 121 couples the ablation controller 180 to a fluid lumen of the shaft 124 for transporting a cooled fluid between the ablation controller 180 and ablation tip 130. In other embodiments, the connector can electrically couple the ablation subsystem 180 (also referred to as the ablation controller) to a lead wire that extends via a lumen through the shaft, thereby providing an electrical current to drive ablation therapies conducted by an electrode transmitter at the ablation catheter tip 130 (e.g., radio frequency, ultrasound, and laser ablation therapies).

In specific embodiments, ablation catheter tip 130 can include pressure sensors and/or contact sensors that communicate with ablation subsystem 180. When the pressure sensor, for example, indicates contact with myocardial tissue, the ablation controller can automatically initiate an ablation therapy for a pre-set time and intensity. Where the ablation catheter tip is prematurely withdrawn from the myocardial tissue, prior to completion of the ablation therapy at that location, the ablation controller will pause the ablation procedure and provide an indication to the clinician of the incomplete ablation. In further more specific embodiments, the ablation controller 180 can communicate with a localization system to indicate and display locations of completed ablation therapies on models used for displaying the position of the ablation catheter tip 130 within the cardiac muscle.

Connector 121 can provide mechanical, electrical, and/or fluid connections for cables extending from other components in catheter system 100, such as, for example, a fluid source (when ablation catheter 160 comprises an irrigated catheter) and contact/pressure sensing circuitry. The connector 121 being disposed at the proximal end 126 of the ablation catheter. Various electrical and mechanical connection methodologies are well known in the art.

In many ablation catheter embodiments, irrigation at ablation catheter tip 130 is desirable to cool the catheter tip 130 to avoid temperatures that could cause coagulation, and otherwise remove and prevent the pooling of blood on and in proximity thereto. Such blood coagulation is often caused by the emission of energy from the ablation catheter tip 130 during the ablation therapy, and irrigation during the ablation therapy cools the catheter tip in proximity thereto, preventing coagulation in proximity to the ablation catheter tip 130.

Handle 122 provides a location for a clinician to hold ablation catheter 160, and control the axial movement of the catheter within the vasculature of the patient and to further steer or otherwise guide catheter shaft 124 within the patient's body 140 to a target location for the ablation therapy. For example, the handle 122 can include means to manipulate one or more steering wires extending through the ablation catheter to a distal end 128 of the shaft to steer the shaft 124, and as a result ablation catheter tip 130. The handle 122 and steering means thereof are conventional in the art and it will be understood that the construction of the handle can vary. In other ablation catheter embodiments, control of the catheter can be automated by robotics, or controlled by a magnetic-based guidance system.

As shown in FIG. 1, representative shaft 124 is an elongated, tubular, and flexible member configured for movement within a patient's body 140. The shaft 124 supports ablation catheter tip 130 at a distal end 128 of ablation catheter 160. The shaft 124 can also permit transport, delivery and/or removal of fluids (including irrigation fluids, cryogenic ablation fluids, and body fluids), medicines, and/or surgical tools or instruments. The shaft, which can be made from conventional materials used for catheters, such as polyurethane, defines one or more lumens configured to house and/or transport electrical conductors, fluids, and/or surgical tools. The ablation catheter can be introduced into a blood vessel or other structure within the body through a conventional introducer.

In an exemplary ablation therapy, to correct for atrial arrhythmia, the introducer is introduced through a peripheral vein (typically a femoral vein) and advanced into a right atrium of a cardiac muscle. In a transseptal approach to reach the left atrium, the introducer then makes an incision in the interatrial septum (the tissue wall between the left and right atriums), typically at the fossa ovalis, and extends through the incision in the fossa ovalis to anchor the introducer in the fossa ovalis. Ablation catheter 160 can then be extended through a lumen of the introducer into the left atrium of the cardiac muscle. Shaft 124 of the ablation catheter can then be steered or guided through the left atrium to position an ablation catheter tip 130 into a desired location within the left atrium such as a pulmonary vein.

During cardiac ablation therapy, it is desirable to precisely position ablation catheter tip 130 circumferential to either an antral or proximal ostia of a target pulmonary vein around which the ablation therapy is to take place. Precise positioning of the ablation catheter tip is particularly difficult in many embodiments due to the transseptal approach through the fossa ovalis which causes catheter shaft 124 to be naturally biased away from the pulmonary veins. This bias places an additional torque on ablation catheter system 100, which can result in the ablation catheter tip, after placement in contact with myocardial tissue proximal the target pulmonary vein, to bias away from contact with the tissue (where proper force on the steering wires, for example, is not maintained during the therapy). At locations of the resulting lesion line (from the ablation therapy), where the shaft 124 is required to make the smallest radius, the shaft can exhibit decreased force on the tissue with a similar steering input from the clinician. As a result, the ablation therapy efficacy can be uneven along the lesion line.

Aspects of the present disclosure improve the efficacy of ablation therapy by implementing subelectrodes within ablation catheter tip 130 to identify sources of arrhythmias, and/or to provide real-time feedback regarding the efficacy of an ablation. Specifically, the impedance of measured tissue is indicative of the efficacy of an ablation therapy (e.g., size and consistency of newly formed lesion). Where an ablation therapy at a specific location was not sufficiently effective, an additional therapy application can be applied without removing the ablation catheter tip from the target tissue to conduct electrophysiological measurements with a separate electrophysiology catheter.

Ablation subsystem 180 may further receive and process the electrical signals (e.g., electrograms (EGM) from various subelectrodes within ablation catheter tip 130. The resulting EGM data may be further recorded by the ablation subsystem 180 and provide time-wise EGM data indicative of changes to the electrical signals experienced at the location of the subelectrodes (e.g., within the heart, and/or at an antral portion or ostia of a pulmonary vein). Aspects of the present disclosure related to systems and methods for receiving and processing EGM data, and generating electrophysiology maps based on such data is further disclosed in, for example, U.S. Pat. Nos. 9,220,435 and 8,620,978, which are hereby incorporated by reference as though fully set forth herein.

Figure 2:
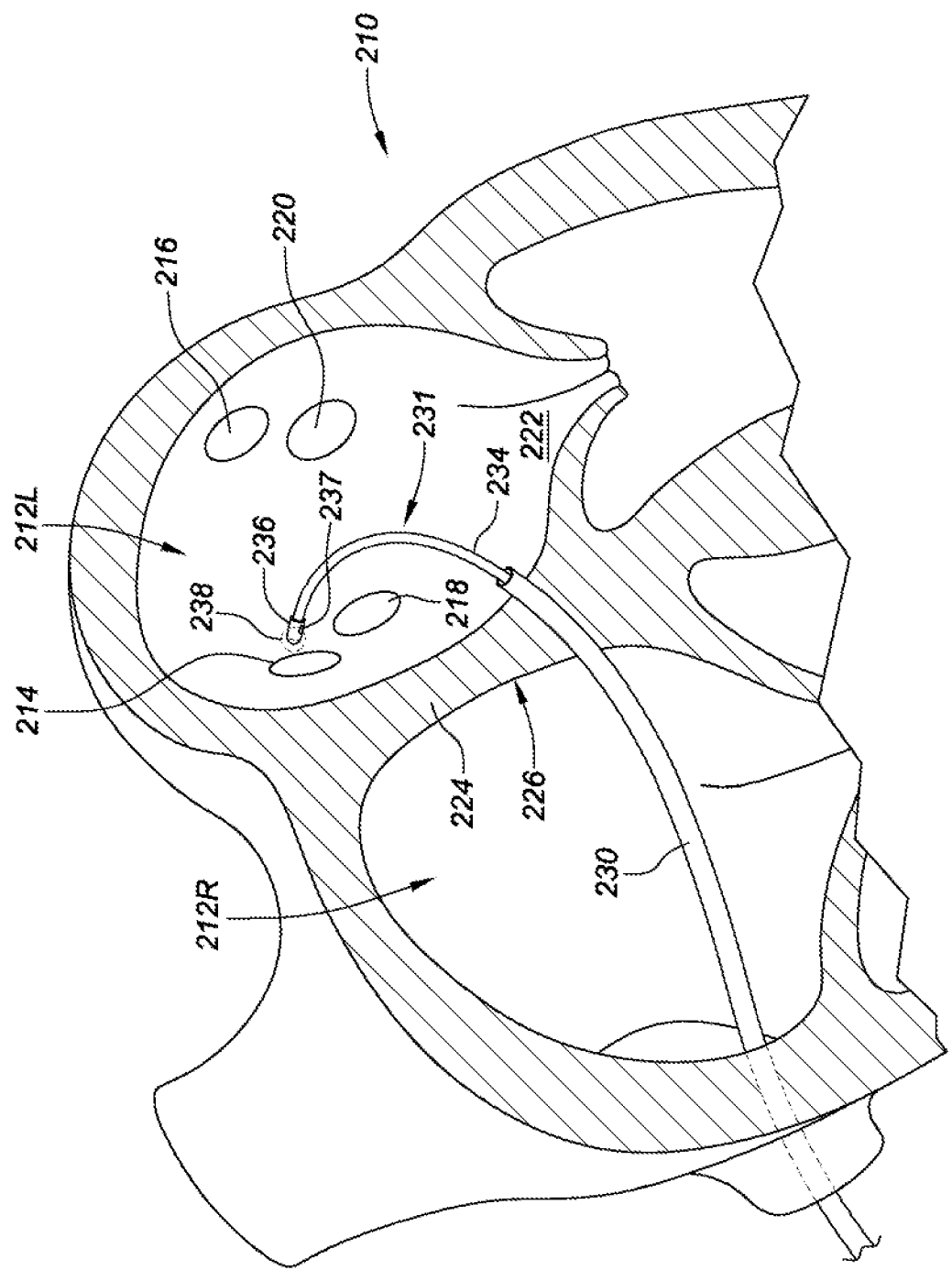
FIG. 2 is a partial cross-sectional front view of a left and right atrium of a cardiac muscle with an ablation catheter in contact with myocardial tissue in proximity to an antral portion of a pulmonary vein, consistent with various aspects of the present disclosure.

As shown in FIG. 2, an ablation catheter 231 as described herein can be introduced into any chamber of the heart to ablate targeted tissue. For example, the ablation catheter 231 can be introduced into a left atrium 212L of a cardiac muscle 210 by an introducer 230. A steerable portion of the catheter shaft 234 can guide ablation catheter tip 236, once introduced into the left atrium by the introducer. The ablation catheter includes one or more electrophysiology mapping electrodes 237 at a distal end of the ablation catheter 231. In operation, the introducer has its distal end positioned within left atrium and anchored via a transseptal puncture. As shown in FIG. 2, a transseptal approach can be utilized in which the introducer is introduced through a peripheral vein (typically a femoral vein) and advanced into right atrium 212R of the cardiac muscle. The introducer makes a small incision into fossa ovalis 226 which allows the distal end of the introducer to enter the left atrium and to anchor itself to a wall 224 of the fossa ovalis.

Ablation catheter 231 can also be introduced into left atrium 212L through the arterial system. In such a case, introducer 230 is introduced into an artery (such as a femoral artery) and advanced retrograde through the artery to the aorta, the aortic arch, and into the left ventricle. The ablation catheter is then extended from within a lumen of the introducer to enter the left atrium through mitral valve 222. Once the introducer is positioned within the left atrium, steerable ablation catheter 231 is advanced out of a distal end of the introducer and toward one or more pulmonary veins (e.g., 214, 216, 218, and 220). As shown in FIG. 2, the target pulmonary vein is right superior pulmonary vein 214. Steerable catheter portion 234 is manipulated by the clinician until a distal tip of the ablation catheter is in contact with a desired ablation location 238, or target tissue (e.g., in proximity to an antral portion of the pulmonary vein 214), after which the target tissue receives ablation therapy which forms a lesion that impedes the flow of electrons between the pulmonary vein and the left atrium.

To ablate the tissue, once in contact with target tissue 238, ablation catheter tip 236 can electrically conduct a DC energy current into the targeted tissue. In other embodiments, the ablation catheter tip can transmit radiofrequency energy to ablate the target tissue. In yet other embodiments, the ablation catheter can deliver one or more of the following energies to the targeted tissue: cryoablation, laser, chemical, and high-intensity focused ultrasound, among others. Some embodiments can utilize more than one type of ablation therapy. This process is repeated, typically in a circular fashion around the periphery of the antral portion of the pulmonary vein to form a lesion line that substantially blocks all the erratic electrical signals emanating from the targeted pulmonary vein. It should be understood, however, that the catheter ablation system can find application in connection with a variety of other tissues within human and non-human bodies, and therefore, the present disclosure is not meant to be limited to the use of the catheter ablation system in connection with only cardiac tissue (e.g., pulmonary veins) and/or human bodies.

Electrophysiological electrodes 237 (e.g., electrical mapping electrodes), near the distal tip of ablation catheter 231 allows the clinician to perform an electrical mapping of the conduction potential of the pulmonary vein before and after (and potentially during) an ablation therapy at target tissue 238 to provide data related to the efficacy of the ablation therapy. Moreover, the mapping electrodes can be used to diagnose the source of an atrial arrhythmia, which can then be used to focus the target location(s) of the ablation therapy. This electrical mapping is critical to the success of the procedure as the clinician is able to determine throughout the ablation therapy the improvement in electrical signal blockage. Accordingly, during an ablation therapy procedure the clinician can make informed decisions as to the need for additional tissue ablation to provide a desired signal blockage.

Figure 3:
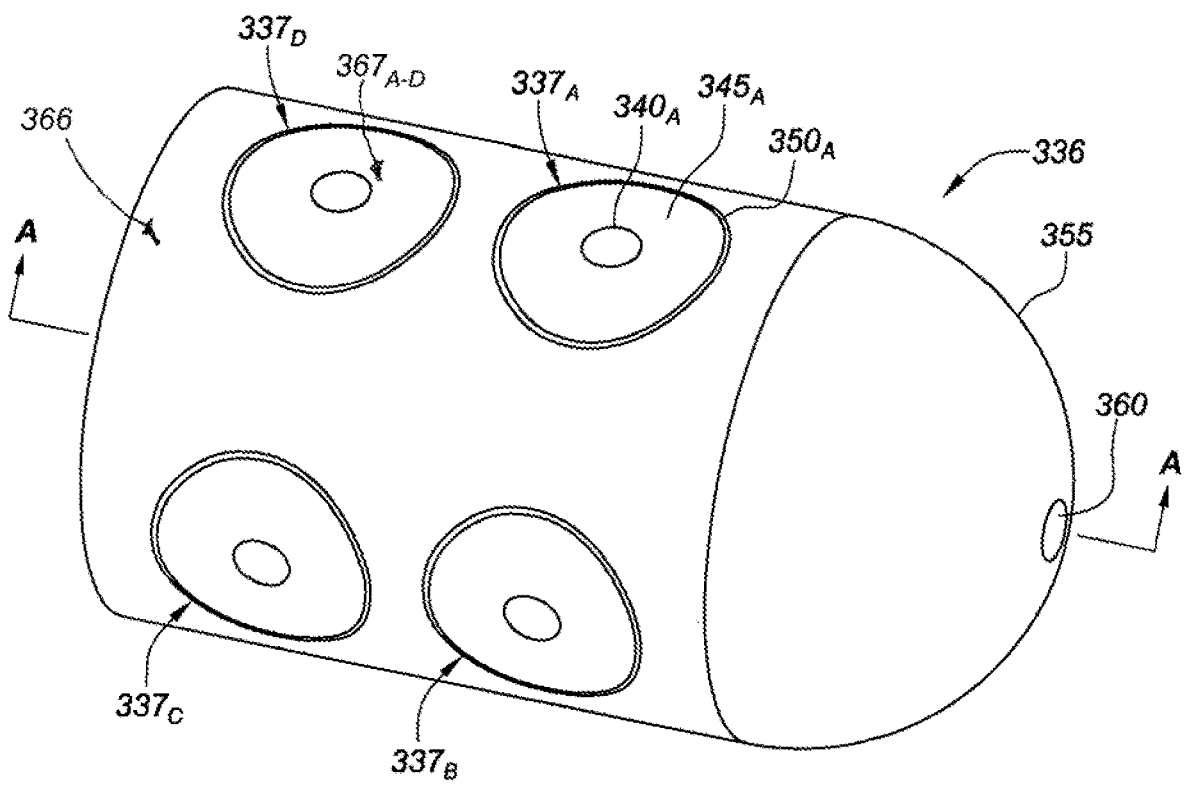
FIG. 3 is an isometric view of an ablation catheter tip, consistent with various aspects of the present disclosure.

FIG. 3 is an isometric view of an ablation catheter tip 336, consistent with various aspects of the present disclosure. The ablation catheter tip includes an electrode 355 for conducting tissue ablation therapy using, for example, radio frequency, or high-intensity focused ultrasound. The ablation catheter tip can include one or more irrigant port 360 to provide irrigant such as a saline solution in proximity to the electrode 355. Proximal to the electrode 355, the ablation catheter tip 336 includes one or more subelectrodes 337$_{A-D}$, which can be distributed in any desired fashion, such as circumferentially and linearly distributed, about the ablation catheter tip 336. Subelectrode housing 345$_A$ surrounds subelectrode receiver 340$_A$, and provides a mounting point to the ablation catheter tip 336. Subelectrodes 337$_{B-D}$ may also have similar structures. Insulating material 350, such as a biocompatible material, can be utilized to couple the subelectrodes 337$_{A-D}$ to the ablation catheter tip 336, while providing electrical insulation, and in some cases also providing thermal insulation, from the energy being transmitted by the electrode 355.

Each of subelectrodes 337$_{A-D}$ can function as electrophysiology sensors, allowing each subelectrode to receive a signal indicative of electrical signals traveling through myocardial tissue in proximity to the subelectrode (the electrical signal data may be indicative of calorimetry, for example). In further embodiments, the subelectrodes can also emit electrical pulses to initiate a cardiac arrhythmia, or to determine the impedance across a lesion which is straddled by two subelectrodes (one emitting an electrical signal and the other receiving the signal). When operated in conjunction, the subelectrodes can simultaneously map electrophysiology of an area of the cardiac muscle (e.g., an antral perimeter of a pulmonary vein). Such an electrophysiology map can identify areas near a pulmonary vein where additional ablation therapy is required, or as discussed above, to diagnose a source of the electrical signals causing a cardiac arrhythmia, prior to conducting ablation therapy.

In various embodiments of the present disclosure, subelectrodes 337$_{A-D}$ on ablation catheter tip 336 can be circumferentially and linearly distributed about the ablation catheter tip 336. In one example embodiment, one or more subelectrodes 337 may be linearly aligned along a longitudinal length of the catheter tip 336, and/or radially offset from one another relative to a longitudinal axis of the catheter tip 336. In one specific embodiment, the subelectrodes 337 may be positioned about the catheter shaft in a spiral or helical formation. Various orientations and patterns of the subelectrodes 337 along a diameter of the ablation catheter tip 336, as well as various quantities of subelectrodes can be utilized. In one example embodiment, where the subelectrode(s) 337 are only utilized for emitting electrical pulses to initiate a cardiac arrhythmia, a single subelectrode can be sufficient. In other embodiments, such as those utilizing the subelectrodes for electrophysiology mapping, and/or to determine an impedance across tissue, at least two subelectrodes may be required.

In many embodiments of the present disclosure, subelectrodes 337$_{A-D}$ are positioned opposite one another relative to a longitudinal axis of ablation catheter tip 336. By positioning the subelectrodes 337 opposite one another, the subelectrodes can take measurements that effectively map the entire ablated tissue region. Such measurements expedite the surgical procedure, and can further obviate the need for secondary catheters (e.g., electrophysiology mapping catheters), and removal of the ablation catheter tip 336 from the ablation location prior to confirmation that the ablated tissue is effectively isolating electrical signals traveling there through.

In one embodiment, the subelectrodes 337 are cut into, and set substantially flush with the tip shell surface, or more particularly are substantially flush with the sidewall of the ablation catheter tip 336. In the present context, flush may be defined as being level or even with another surface. In other words, the tip shell surface and a top surface of the subelectrodes 337 have no substantial change in elevation. In this manner, the ablation catheter tip 336 is constructed to have an atraumatic tip for safety and ease of use.

In many embodiments, close proximity between subelectrodes 337$_{A-D}$ and electrode 355 is desirable. For example, in embodiments where it is desirable for the subelectrodes 337 to conduct electrophysiological mapping, impedance measuring, among other data collection techniques, without moving the electrode 355 away from the ablated tissue. Benefits of such an embodiment include ablating tissue and determining the resulting electrical signal blocking across the ablated tissue without moving the catheter tip 336 from the location of the ablated tissue. Where the catheter tip 336 must be re-located to position an electrophysiology catheter (or electrophysiology electrodes) proximal the ablated tissue, valuable surgical time is consumed re-positioning the ablation catheter tip 336 where it is determined that the ablated tissue requires additional ablation therapy to achieve sufficient electrical isolation. Accordingly, aspects of the present disclosure are also directed to positioning one or more subelectrodes 337 upon an exterior surface of the electrode 355, at a distal end of the catheter tip 336. In such embodiments, the electrode and subelectrode(s) configuration can enable real-time updates as to the effectiveness of an ablation therapy while the ablation is occurring, minimizing the risk for damaging nearby nerves and other arteries, as well as limiting scar-tissue formation within a target tissue (e.g., pulmonary vein) to only that necessary to achieve electrical isolation.

As shown in FIG. 3, a top surface 367$_{A-D}$ of subelectrodes 337 and subelectrode housings 345$_{A-D}$ are set substantially even or flat with tip shell surface 366. However, in various embodiments, not all of the top surfaces 367$_{A-D}$ of subelectrodes 337 and subelectrode housings 345$_{A-D}$ need be positioned substantially even with the tip shell surface 366.

Figure 4:
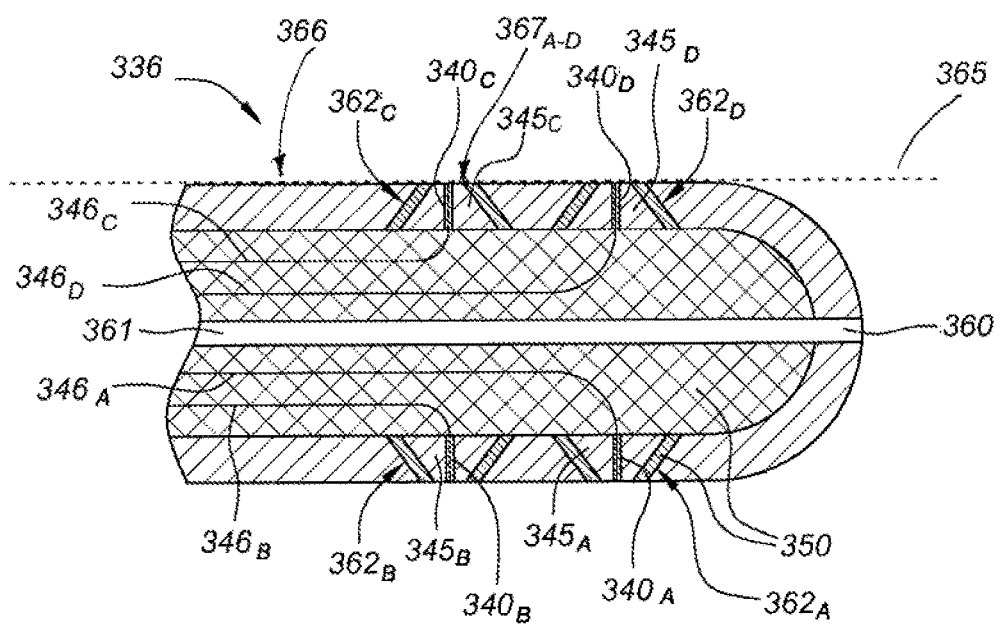
FIG. 4 is a longitudinal cross-sectional top view of the ablation catheter tip of FIG. 3, consistent with various aspects of the present disclosure.

FIG. 4 is a longitudinal cross-sectional top view of the representative ablation catheter tip 336 of FIG. 3. As shown in FIG. 4, the ablation catheter tip is a shell with a number of conical-shaped apertures 362$_{A-D}$ extending from an interior surface to an exterior surface of the ablation catheter tip. Conical frustum shaped subelectrode housings 345$_{A-D}$, with electrode receivers 340$_{A-D}$ encompassed therein, can be inserted into the conical apertures 362$_{A-D}$ of the ablation catheter tip from within. The subelectrode housings are coupled to the ablation catheter tip with an insulator to insulate the subelectrodes from the remaining portion of the ablation electrode. The insulator may be a biocompatible material 350 (e.g., electrically and/or thermally insulating potting material). Lead wires 346$_{A-D}$ extend from each subelectrode to a proximal end of the catheter shaft, and provide electrical signals, indicative of the electrophysiological characteristics of the myocardial tissue in proximity to each of the subelectrodes, to mapping controller circuitry. Additional potting material may be used to fill the remainder of the interior of the ablation electrode tip shell to further secure the subelectrodes.

Irrigant port 360 receives irrigant from irrigant lumen 361, which extends between a distal and proximal end of the catheter shaft.

Due to the severe, and repeated, thermal extremes associated with ablation catheters, coupling subelectrodes to an ablation catheter tip could exhibit unacceptable failure rates which can result in the discharge of the subelectrodes from the ablation catheter tip during an ablation therapy procedure. Such discharge during ablation therapy can be hazardous to the patient, and even result in death. Aspects of the present disclosure prevent discharge of these subelectrodes due to the complimentary conical shape of the aperture 362 and the conical frustum shaped subelectrode housing 345. Specifically, an outer diameter of the conical aperture is smaller than an interior diameter of the subelectrode housing; accordingly, even if the insulating, biocompatible material used to couple the subelectrodes to the ablation catheter tip degrades, the subelectrode will not have the physical clearance to discharge itself from the conical aperture.

Subelectrode housings $345_{A-D}$ and paired apertures $362_{A-D}$ in ablation catheter tip 336 may also be formed of other shapes, a combination of shapes, and/or complex shapes. For example, aspects of the present disclosure are directed to any shape wherein the subelectrode housing 345 may be installed from an interior portion within the ablation catheter tip 336, have a surface that is in contact with an environment exterior to the ablation catheter (to allow for sensing of such an environment, and tissue in contact therewith), and wherein the shape of the subelectrode housing 345 and the mated aperture causes a physical interference that prevents the movement of the subelectrode housing (and electrode receivers $340_{A-D}$ therein) external to the ablation catheter tip 336.

In various other embodiments, apertures $362_{A-D}$ in ablation catheter tip 336 may be a basic circular aperture, with subelectrode housings $345_{A-D}$ including lips at a proximal portion of the subelectrode housings, wherein the lip includes a larger outer diameter than an inner diameter of the mating aperture. In response to a degradation of biocompatible material 350 between a subelectrode housing 345 and an aperture of the ablation catheter tip 336, electrode receiver 340 within the subelectrode housing may not discharge from within the catheter tip, due to the interference between the lip and the aperture. In a similar embodiment, the aperture may include a lip wherein the subelectrode housing extends into a portion of the aperture during installation and is seated against the lip. The lip being a portion of the aperture with an inner diameter that is less than the outer diameter of at least a portion of the subelectrode housing 345.

In one example embodiment, a subelectrode housing 345 includes a male thread extending along at least a portion of its outer diameter, and a mating aperture 362 within ablation catheter tip 336 includes female threads along at least a corresponding portion of its inner diameter. In some embodiments, the threads on either the subelectrode housing, the aperture, or both may cease prior to reaching an exterior facing surface, thereby preventing the subelectrode housing (and electrode receiver 340 within the housing) from discharging from within the ablation catheter tip during an operation. When assembled, a subelectrode housing can be threaded into an aperture of the ablation catheter tip from within an interior portion of the tip, and may be glued, welded, or otherwise prevented from dethreading from one another. In yet other embodiments, the subelectrode housings $345_{A-D}$ and mating apertures within ablation catheter tip 336 may be snap-fit together, press-fit, metal welded, ultrasonically welded, chemically welded, or otherwise coupled to one another using one of the means discussed herein, or a combination thereof.

Various other combinations of structural features on either ablation catheter tip 336 and/or subelectrode housings $345_{A-D}$ to maintain the electrode receivers $340_{A-D}$ within the ablation catheter tip are also contemplated. In one embodiment, an aperture 362 of ablation catheter tip 336 and/or subelectrode housing 345 can include an interfering member or feature that prevents the subelectrode housing from extending out of the ablation catheter tip 336.

Various methodologies can be utilized to form conical apertures $362_{A-D}$ within ablation catheter tip shell, and/or the other various interacting members and features, as discussed above, to prevent the discharge of the subelectrode housing 345 and electrode receiver 340 from the ablation catheter tip 336; for example, laser cutting, milling, water jetting, among other manufacturing techniques well known in the art (and those discussed in detail above).

As shown in FIG. 4, an imaginary line 365 substantially contacts and extends across a tip shell surface 366 and a top surface $367_{A-D}$ of subelectrode receivers $340_{A-D}$ and subelectrode housings $345_{A-D}$.

In one embodiment, a laser is employed to define the subelectrodes in a metal shell catheter tip, where the laser slotting is at an angle to the shell surface so the defined electrodes cannot fall out. The laser may cut the channels for the subelectrodes at an angle to prevent the subelectrodes from falling out of the catheter tip. In one embodiment, the angle is cut at approximately 30 degrees to 45 degrees to the tip surface.

In one example embodiment, a metal RF ablator tip with a general shell shape is disclosed. The shell including a plurality of subelectrodes distributed about the tip and employed in either a unipolar or bipolar configuration. In a unipolar configuration (also referred to as monopolar configuration), two subelectrodes work in conjunction with one another, a first subelectrode placed in proximity to an area of interest (e.g., target tissue, ablation lesion, etc.), while a second subelectrode is placed away from the area of interest and utilized as a reference electrode (e.g., a body patch). In specific implementations of a unipolar configuration, the signal between the two subelectrodes is amplified and recorded. In a bipolar configuration, two subelectrodes are placed in proximity to the area of interest, with a third subelectrode being placed away from the area of interest and utilized as a reference electrode. The signal between the two subelectrodes in proximity to the area of interest is amplified differentially with respect to the reference electrode. Such a bipolar configuration may reduce or eliminate common noise between the two subelectrodes, thereby delivering an improved signal.

In one embodiment, holes for subelectrode leads/connectors are created, such as by laser drilling the holes, and the leads are inserted into the holes. The subelectrodes are held from the inside of the shell during lasering, such as by filling the shell interior in a manner that attaches to the future site of the kerfed subelectrodes and captures or "pots" the internal leads. This allows the subelectrode kerfs to be formed next with the formed subelectrodes still being held in place. The actual laser kerfs can then be filled from the outside. After lasering and being epoxied in place (e.g., the laser cuts filled with epoxy or other electrically insulating material), the subelectrodes may be released from the inside, and a permanent shell filler member or material can be provided through which the subelectrode wires are fed.

In another embodiment, a catheter tip is provided that includes at least an ablation electrode and at least one subelectrode. In this embodiment, the ablation electrode includes a shell defining an internal cavity, and includes at least one angled aperture formed in the shell with an internal aperture diameter larger than an external aperture diameter. The catheter tip further includes a subelectrode having a conical shape that is complementary to the angled aperture formed in the shell to enable the subelectrode to be seated into the angled aperture from the internal cavity. In this manner, the subelectrode is physically unable to move externally out of the catheter tip shell. In more particular embodiments of such a catheter tip, an electrical insulator may be positioned between the conical shape of the subelectrode and the angled aperture formed in the shell to electrically insulate the ablation electrode from the subelectrode. In yet another particular embodiment of such a catheter tip, an electrically insulating material may couple the subelectrode to the angled aperture, where the subelectrode is substantially flush with the external surface of the shell when seated into and coupled to the angled aperture. In some embodiments, the electrically insulating material is a biocompatible material, and in still other embodiments the material may also be thermally insulating.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Based upon the above discussion and illustrations, those skilled in the art will readily recognize that various modifications and changes may be made to the various embodiments without strictly following the exemplary embodiments and applications illustrated and described herein. For example, subelectrodes consistent with various aspects of the present disclosure need not be conical frustum shaped, nor do the apertures which contain the subelectrodes need to be conical. Instead, the shape of the subelectrodes and apertures may be any combination of shapes that prevent the subelectrodes from escaping from the apertures in the ablation catheter tip. Such modifications do not depart from the true spirit and scope of various aspects of the disclosure, including aspects set forth in the claims.

What is claimed is:

1. An ablation catheter tip comprising: a tissue ablation electrode including a shell portion defining an internal cavity, and a plurality of apertures that extend from an interior surface of the shell portion to an exterior surface of the shell portion; a plurality of conical-frustum shaped subelectrodes, each of the subelectrodes including a receiver surface and being seated within one of the plurality of apertures within the tissue ablation electrode; and an insulating material coupling the tissue ablation electrode to each of the plurality of subelectrodes; wherein the plurality of apertures have a complimentary conical shape to the plurality of subelectrodes; and wherein the plurality of subelectrodes are configured and arranged to receive electrical signals indicative of electrophysiological characteristics of myocardial tissue in proximity to each of the subelectrodes.

2. The ablation catheter tip of claim 1, further comprising an irrigant port at a distal end of the ablation catheter tip; an irrigant lumen, coupled to the irrigant port, that extends from a proximal to a distal end of the tissue ablation electrode through the internal cavity; and wherein the internal cavity of the tissue ablation electrode is filled with a potting material.

3. The ablation catheter tip of claim 1, wherein the plurality of subelectrodes include four subelectrodes coupled to the tissue ablation electrode and longitudinally dispersed relative to an axis of the ablation catheter tip, pairs of the plurality of subelectrodes configured in bipolar combinations.

4. The ablation catheter tip of claim 1, wherein the plurality of subelectrodes are configured in bipolar combinations.

5. The ablation catheter tip of claim 1, wherein the receiver surface of the subelectrodes are flush with an exterior surface of the tissue ablation electrode.

6. The ablation catheter tip of claim 1, wherein each of the subelectrodes are electrically coupled to an internal lead that extends through the internal cavity of the tissue ablation electrode, and each of the apertures are circumferentially distributed about an axis of the tissue ablation electrode.

7. An ablation catheter comprising: a flexible catheter body having a distal portion; a tissue ablation electrode tip including an internal cavity and a plurality of apertures distributed about an axis of the tissue ablation electrode tip and extending from an exterior surface of the tissue ablation electrode tip into the internal cavity, and wherein the tissue ablation electrode tip is coupled to the distal portion of the flexible catheter body, and configured and arranged to transmit radio frequency energy to myocardial tissue in proximity to the tissue ablation electrode tip and thereby ablate the myocardial tissue; and a plurality of subelectrodes, each of the subelectrodes are configured and arranged to be seated within one of the apertures in the tissue ablation electrode tip, extend through a portion of the tissue ablation electrode tip to the internal cavity, and are configured and arranged to receive electrical signals indicative of electrophysiological characteristics of the myocardial tissue in proximity to each of the subelectrodes; wherein one or more of the plurality of apertures have a conical shape and one or more of the plurality of subelectrodes have a conical-frustum shape, the one or more of the plurality of apertures and the one or more of the plurality of subelectrodes having complimentary tapers in the range of 30-45 degrees; wherein a receiver surface of the subelectrodes is flush with the exterior surface of the tissue ablation electrode tip.

8. The ablation catheter of claim 7, wherein the subelectrodes are electrically and thermally insulated from the tissue ablation electrode tip.

9. The ablation catheter of claim 7, wherein the subelectrodes are mechanically coupled to the tissue ablation electrode tip with a biocompatible material.

10. The ablation catheter of claim 9, wherein the biocompatible material thermally and electrically isolates the subelectrodes from the tissue ablation electrode tip.

11. The ablation catheter of claim 7, further including thermal insulation between the subelectrodes and the tissue ablation electrode tip, the thermal insulation is configured and arranged to allow the subelectrodes to receive and output signals indicative of calorimetry.

12. The ablation catheter of claim 7, wherein a shape of the subelectrodes and one or more surfaces of the apertures are configured and arranged to prevent the subelectrodes from decoupling from the tissue ablation electrode tip.

13. The ablation catheter of claim 7, wherein the subelectrodes are coupled to the tissue ablation electrode tip in a unipolar manner.

14. The ablation catheter of claim 7, wherein the subelectrodes are configured in bipolar combinations.

15. The ablation catheter of claim 7, further comprising an irrigant port extending through a distal end of the tissue ablation electrode tip, and an irrigation lumen coupled to the irrigant port and extending through the tissue ablation electrode tip and flexible catheter body to a proximal end of the flexible catheter body.

16. The ablation catheter of claim 7, further comprising an irrigant port extending through a distal end of the tissue ablation electrode tip, and an irrigation lumen coupled to the irrigant port and extending through the tissue ablation electrode tip and flexible catheter body to a proximal end of the flexible catheter body, and wherein portions of the irrigant port, irrigation lumen, and the subelectrodes within the apertures cavity of the tissue ablation electrode tip are potted with a biocompatible material.

17. The ablation catheter tip of claim 7, wherein the sub electrodes are coupled to and electrically isolated from the tissue ablation electrode tip by electrically insulative material configured and arranged to insulate the subelectrodes from the radiofrequency energy transmitted through the tissue ablation electrode tip.

18. The ablation catheter of claim 7, further comprising internal leads that extend a length of the flexible catheter body and electrically couple the subelectrodes to a proximal portion of the ablation catheter, the internal leads configured and arranged to transmit signals to the proximal portion of the ablation catheter indicative of the electrophysiological characteristics of the myocardial tissue in proximity to the subelectrode.

19. A catheter tip comprising: an ablation electrode comprising a shell defining an internal cavity, and at least one conically shaped aperture formed in the shell with an internal aperture cross-section larger than an external aperture cross-section; and a subelectrode having a conical-frustum shape complementary to the aperture formed in the shell, the subelectrode configured and arranged to be seated into the aperture formed in the shell; wherein the subelectrode is configured and arranged to receive electrical signals indicative of electrophysiological characteristics of myocardial tissue in proximity to the subelectrode.

20. The catheter tip of claim 19, further comprising an electrical insulator positioned between the subelectrode and the angled aperture, the electrical insulator configured to electrically insulate the ablation electrode from the subelectrode.

21. The catheter tip of claim 19, further comprising an electrically insulating material coupling the subelectrode to the aperture, wherein the subelectrode is flush with an external surface of the shell when seated in the angled aperture.

22. The catheter tip of claim 21, wherein the insulating material comprises a biocompatible insulating material.

\* \* \* \* \*